United States Patent
DeLuca et al.

(10) Patent No.: US 6,281,249 B1
(45) Date of Patent: *Aug. 28, 2001

(54) 18-SUBSTITUTED-19-NOR-VITAMIN D COMPOUNDS

(75) Inventors: Hector F. DeLuca, Deerfield; Zu Y. Cai, Madison, both of WI (US)

(73) Assignee: Wisconsin Alumni Research Foundation, Madison, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/353,866

(22) Filed: Jul. 15, 1999

Related U.S. Application Data

(62) Division of application No. 08/897,553, filed on Jul. 21, 1997, now Pat. No. 5,939,406.

(51) Int. Cl.[7] .......................... G07C 401/00; A61K 31/59
(52) U.S. Cl. .......................... 514/675; 514/675; 568/309
(58) Field of Search .............................. 568/309; 514/675

(56) References Cited

U.S. PATENT DOCUMENTS 5,246,925  9/1993  DeLuca et al. ................. 514/167

(List continued on next page.)

FOREIGN PATENT DOCUMENTS

| 0078704 | 4/1987 | (EP) . |
| WO 90/09991 | 9/1990 | (WO) . |
| WO 96/16035 | 5/1996 | (WO) . |

OTHER PUBLICATIONS

Baggiolini et al. (J. Org. Chem. (1986), 51, 3098–3108), 1996.*

(List continued on next page.)

*Primary Examiner*—Sabiha Qazi
(74) *Attorney, Agent, or Firm*—Andrus, Sceales, Starke & Sawall, LLP

(57) ABSTRACT

This invention provides a novel class of vitamin D compounds, namely, 13-ethyl and 13-vinyl-18,19-dinor-vitamin D derivatives, as well as a general method for their chemical synthesis. The compounds have the formula:

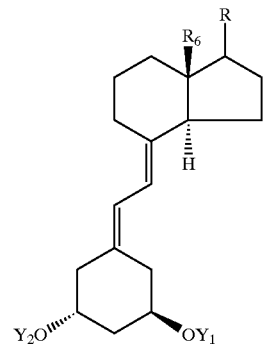

where $Y_1$ and $Y_2$, which may be the same or different, are each selected from the group consisting of hydrogen and a hydroxy-protecting group, $R_6$ is selected from the group consisting of an ethyl or vinyl radical, and where the group R represents any of the typical side chains known for vitamin D type compounds. These 18-substituted compounds are characterized by minimal intestinal calcium transport activity and minimal bone calcium mobilization activity resulting in novel therapeutic agents for the treatment of secondary hyperparathyroidism. These compounds also exhibit pronounced activity in arresting the proliferation of undifferentiated cells and inducing their differentiation to the monocyte thus evidencing use as anti-cancer agents and for the treatment of diseases such as psoriasis.

6 Claims, 2 Drawing Sheets

U.S. PATENT DOCUMENTS

| | | | |
|---|---|---|---|
| 5,403,940 | 4/1995 | Vallés et al. | 549/300 |
| 5,449,668 | 9/1995 | Sestelo et al. | 514/167 |
| 5,587,497 | 12/1996 | DeLuca et al. | 552/653 |
| 5,597,815 | 1/1997 | DeLuca et al. | 514/167 |
| 5,637,742 | 6/1997 | Vallés et al. | 552/653 |

OTHER PUBLICATIONS

Slatopolsky et al, "A New Analog of Calcitriol, 19–Nor–1, 25–$(OH)_2D_2$, Suppresses Parathyroid Hormone Secretion in Uremic Rats in the Absence of Hypercalcemia," *American Journal of Kidney Diseases,* vol. 26, No. 5, Nov., 1995, pp. 852–860.

Nilsson et al, "Synthesis and Biological Evaluation of 18–Substituted Analogs of 1α,25–Dihydroxyvitamin $D_3$," *Inorganic & Medicinal Chemistry Letters,* vol. 3, No. 9, 1993, pp. 1855–1858.

Vallés et al, "Functionalization of Vitamin D Metabolites at C–18 and Application to the Synthesis of 1α, 18, 25–Trihydroxyvitamin $D_3$ and 18,25–Dihydroxyvitamin $D_3$," *Tetrahedron Letters,* vol. 33, No. 11, 1992, pp. 1503–1506.

Maynard et al, "18–Substituted Derivatives of Vitamin D: 18–Acetoxy–1α, 25–Dihydroxyvitamin $D_3$ and Related Analogues," *Journal of Organic Chemistry,* 57, 1992, pp. 3214–3217.

* cited by examiner

18-SUBSTITUTED-19-NOR-VITAMIN D COMPOUNDS

CROSS-REFERENCE TO RELATED APPLICATIONS

This application is a divisional of application Ser. No. 08/897,553, filed Jul. 21, 1997, now U.S. Pat. No. 5,939,406.

STATEMENT REGARDING FEDERALLY SPONSORED RESEARCH OR DEVELOPMENT

This invention was made with United States Government support awarded by the National Institutes of Health (NIH), Grant No. P01-DK14881. The United States Government has certain rights in this invention.

BACKGROUND OF THE INVENTION

This patent invention relates to vitamin D compounds, and more particularly to vitamin D derivatives substituted at the carbon 18 position.

Vitamin D is essential for life in higher animals. It is one of the important regulators of calcium and phosphorus and is required for proper development and maintenance of bone. However, during the past decade, the spectrum of activities promoted by 1,25-$(OH)_2D_3$ has been found to extend far beyond a role in calcium homeostasis. In addition to its action on the intestine, bone, kidney, and parathyroid glands to control serum calcium, this hormone has been shown to have important cell differentiating activity. Ostrem et al, Proc. Natl. Acad. Sci. USA, 84, 2610 (1987). Receptors for this hormone have been identified in several different target cells that respond to 1,25-$(OH)_2D_3$ with a diverse range of biological action. These newly discovered activities have suggested other therapeutic applications of 1,25-$(OH)_2D_3$ including hyperparathyroidism, psoriasis, cancer, and immune regulation.

Secondary hyperparathyroidism is a universal complication in patients with chronic renal failure. Because of its ability to suppress parathyroid hormone (PTH), 1,25-$(OH)_2D_3$ has been used with success in the treatment of secondary hyperparathyroidism, Slatopolsky, et al, "Marked Suppression of Secondary Hyperparathroidism by Intravenous Administration of 1,25-dihydroxycholecalciferol in Uremic Patients", J. Clin. Invest. 74:2136–2143, 1984. Its use is often precluded, however, by the development of hypercalcemia resulting from its potent action on intestinal absorption and bone mineral mobilization.

From the clinical point of view, one of the most difficult biochemical alterations to correct in hemodialysis patients is hyperphosphatemia. Patients on dialysis usually ingest approximately 1.0 to 1.4 grams of phosphorus per day. Since the maximum amount of phosphorus that is removed during each dialysis approximates 800 to 1,000 mg, Hou et al, "Calcium and Phosphorus Fluxes During Hemodialysis with Low Calcium Dialysate", Am. J. Kidney Dis. 18:217–224, 1991, the remaining 2.5 to 3.5 grams of phosphorus ingested per week must be removed by other means. Thus, the use of phosphate binders such as calcium carbonate and calcium acetate are usually utilized to correct the hyperphosphatemia, Emmett et al, "Calcium Acetate Control of Serum Phosphorus in Hemodialysis Patients", Am. J. Kidney Dis. 24:544–550, 1991; Schaefer et al, "The Treatment of Uraemic Hyperphosphataemia with Calcium Acetate and Calcium Carbonate: A Comparative Study", Nephrol Dial Transplant 6:170–175, 1991; Delmez et al, "Calcium Acetate as a Phosphorus Binder in Hemodialysis Patients", J. Am. Soc. Nephrol 3:96–102, 1992. Unfortunately, 1,25-$(OH)_2D_3$ not only increases the absorption of calcium but also of phosphorus, making hyperphosphatemia more difficult to be treated. Thus, the hyperphosphatemia induced in part by the action of 1,25-$(OH)_2D_3$ requires a further addition of calcium carbonate or calcium acetate, which can greatly increase the levels of serum ionized calcium. The high calcium-phosphate product that the patient may develop imposes a tremendous risk for the development of hypercalcemia and metastatic calcifications, Arora et al, "Calcific Cardiomyopathy in Advanced Renal Failure", Arch. Inter. Med. 1335:603–605 1975; Rostand et al, "Myocardial Calcification and Cardiac Dysfunction in Chronic Renal Failure", Am. J. ed. 85:651–657, 1988; Gipstein et al, "Calcification and Cardiac Dysfunction in Chronic Renal Failure", Am. J. Med. 85:651–657, 1988: Gipstein et al, "Calciphylaxis in Man A Syndrome of Tissue Necrosis and Vascular Calcifications in 11 Patients with Chronic Renal Failure", Arch. Intern. Med. 136:1273–1280, 176; Milliner et al, "Soft Tissue Calcification in Pediatric Patients with End-stage Renal Disease", Kidney Int. 38:931–936, 1990. Therefore, the treatment demands a decrease in the amount of 1,25-$(OH)_2D_3$ administered to the patient thus decreasing the effectiveness of 1,25-$(OH)_2D_3$ therapy for controlling PTH secretion. Thus, an analog of 1,25-$(OH)_2D_3$ that can suppress PTH with minor effects on calcium and phosphate metabolism would be an ideal tool for the control of secondary hyperparathyroidism, and the treatment of renal osteodystrophy.

Many structural analogs of 1,25-$(OH)_2D_3$ have been prepared and tested, including 1α-hydroxyvitamin $D_3$, 1α-hydroxyvitamin $D_2$, various side chain homologated $D_3$ and $D_2$ vitamins and fluorinated $D_3$ and $D_2$ analogs. Some of these compounds exhibit an interesting separation of activities in cell differentiation and calcium regulation. This difference in activity may be useful in the treatment of a variety of diseases as renal osteodystrophy, vitamin D-resistant rickets, osteoporosis, psoriasis, and certain malignancies.

Several analogs of 1,25-$(OH)_2D_3$ modified at the carbon 18 position are described in Nilsson et al, "Synthesis and Biological Evaluation of 18-Substituted Analogs of 1α,25-Dihydroxyvitamin $D_3$", Bioorganic and Medicinal Chemistry Letters, Vol. 3, No. 9, pp. 1855–1858, 1993, and their in vitro biological behavior reported. 18-hydroxylated analogs are disclosed in Valles et al, "Functionalization of Vitamin D Metabolites at C-18 and Application to the Synthesis of 1α,18,25-Trihydroxyvitamin $D_3$ and 18,25-Dihydroxyvitamin $D_3$", Tetrahedron Letters, Vol. 33, No. 1, pp. 1503–1506, 1992. 18-acetoxy analogs are described in Maynard et al, "18-Substituted Derivatives of Vitamin D: 18-Acetoxy-1α,25-Dihydroxyvitamin $D_3$ and Related Analogues," J. Org. Chem., Vol. 57, No. 11, pp. 3214–3217, 1992, and are reported to be nearly devoid of in vivo biological activity.

Another class of vitamin D analogs, i.e. the so called 19-nor-vitamin D compounds, are characterized by the replacement of the A-ring exocyclic methylene group (carbon 19), typical of the vitamin D system, by two hydrogen atoms. Biological testing of such 19-nor-analogs (e.g., 1α,25-dihydroxy-19-nor-vitamin $D_3$) revealed a selective activity profile with high potency in inducing cellular differentiation, and very low intestinal calcemic transport activity as well as very low bone calcium mobilizing activity. Thus, these 19-nor compounds are potentially useful as therapeutic agents for the treatment of malignancies, (see U.S. Pat. No. 5,587,497) or the treatment of various skin disorders (see U.S. Pat. No. 5,578,587) as well as for the treatment of hyperphosphatemia (see U.S. Pat. No. 5,597,815), and hyperparathyroidism (see U.S. Pat. No. 5,246,925). Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

Recently, 2-substituted analogs of $1\alpha,25$-dihydroxy-19-norvitamin $D_3$ have also been synthesized, i.e. compounds substituted at 2-position with hydroxy or alkoxy groups (DeLuca et al, U.S. Pat. No. 5,536,713). These compounds exhibit interesting and selective activity profiles making them useful for the treatment of osteoporosis.

SUMMARY OF THE INVENTION

A series of $1\alpha$-hydroxylated vitamin D compounds not known heretofore are the 19-nor-vitamin D analogs having a methyl or methylene group at the 18-position, i.e. 13-ethyl-18,19-dinor-vitamin D compounds and 13-vinyl-18,19-dinor-vitamin D compounds, particularly 13-ethyl-18,19-dinor-$1\alpha,25$-dihydroxyvitamin $D_3$ and 13-vinyl-18,19-dinor-$1\alpha,25$-dihydroxyvitamin $D_3$.

Structurally these novel analogs are characterized by the general formula I shown below:

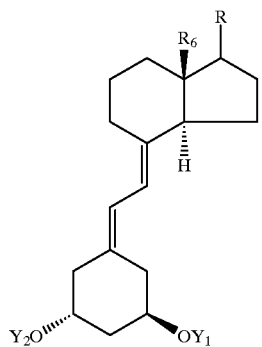

I where $Y_1$ and $Y_2$, which may be the same or different, are each selected from the group consisting of hydrogen and a hydroxy-protecting group, $R_6$ is selected from the group consisting of an ethyl or vinyl radical, and where the group R represents any of the typical side chains known for vitamin D type compounds.

The above novel compounds exhibit a desired, and highly advantageous, pattern of biological activity. These compounds are characterized by little, if any, intestinal calcium transport activity and little, if any, intestinal phosphorus absorption activity, as compared to that of $1\alpha,25$-dihydroxyvitamin $D_3$, as well as little, if any, bone calcium mobilizing activity, as compared to $1\alpha,25$-dihydroxyvitamin $D_3$. At the same time these compounds have the ability to suppress parathyroid hormone (PTH). Hence, these compounds are highly specific in their biological activity. Their preferential activity on suppressing PTH and minimal intestinal calcium transport and bone calcium mobilization activities allows the in vivo administration of these compounds for the treatment of secondary hyperparathyroidism and renal osteodystrophy. Because of their minimal intestinal phosphorus absorption activity, these compounds would be preferred therapeutic agents for the treatment of hyperphosphatemia in kidney disorder patients. The treatment may be transdermal, oral or parenteral. The compounds may be present in a composition in an amount from about 0.1 $\mu$g/gm to about 50 $\mu$g/gm of the composition, and may be administered in dosages of from about 0.1 $\mu$g/day to about 50 $\mu$g/day.

The compounds of the invention are also especially suited for treatment and prophylaxis of human disorders which are characterized by an imbalance in the immune system, e.g. in autoimmune diseases, including multiple sclerosis, diabetes mellitus, host versus graft reaction, and rejection of transplants; and additionally for the treatment of inflammatory diseases, such as rheumatoid arthritis and asthma, as well as the improvement of bone fracture healing and improved bone grafts. Acne, alopecia, skin conditions such as dry skin (lack of dermal hydration), undue skin slackness (insufficient skin firmness), insufficient sebum secretion and wrinkles, and hypertension are other conditions which may be treated with the compounds of the invention.

The above compounds are also characterized by having high cell differentiation activity. Thus, these compounds also provide therapeutic agents for the treatment of psoriasis, or as an anti-cancer agent, especially against leukemia, colon cancer, breast cancer and prostate cancer. The compounds may be present in a composition to treat psoriasis in an amount from about 0.01 $\mu$g/gm to about 100 $\mu$g/gm of the composition, and may be administered topically, transdermally, orally or parenterally in dosages of from about 0.01 $\mu$g/day to about 100 $\mu$g/day.

This invention also provides novel intermediate compounds formed during the synthesis of the end products. Structurally, these novel intermediates have the general formula II shown below:

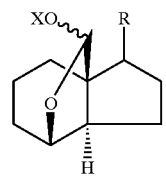

II where R represents any of the typical side chains known for vitamin D type compounds, and X is an acyl group, preferably $CH_3CO$—.

This invention also provides a novel synthesis for the production of the end products of structure I.

This invention also provides a novel efficient synthesis for hydroxylated Windaus Grundmann ketone (8) through four steps from compound (1a) (see Scheme I). Hydroxylated Windaus Grundmann ketone (8) is an important fragment for the synthesis of 25-hydroxy vitamin $D_3$.

DETAILED DESCRIPTION OF THE INVENTION

Figure 1:
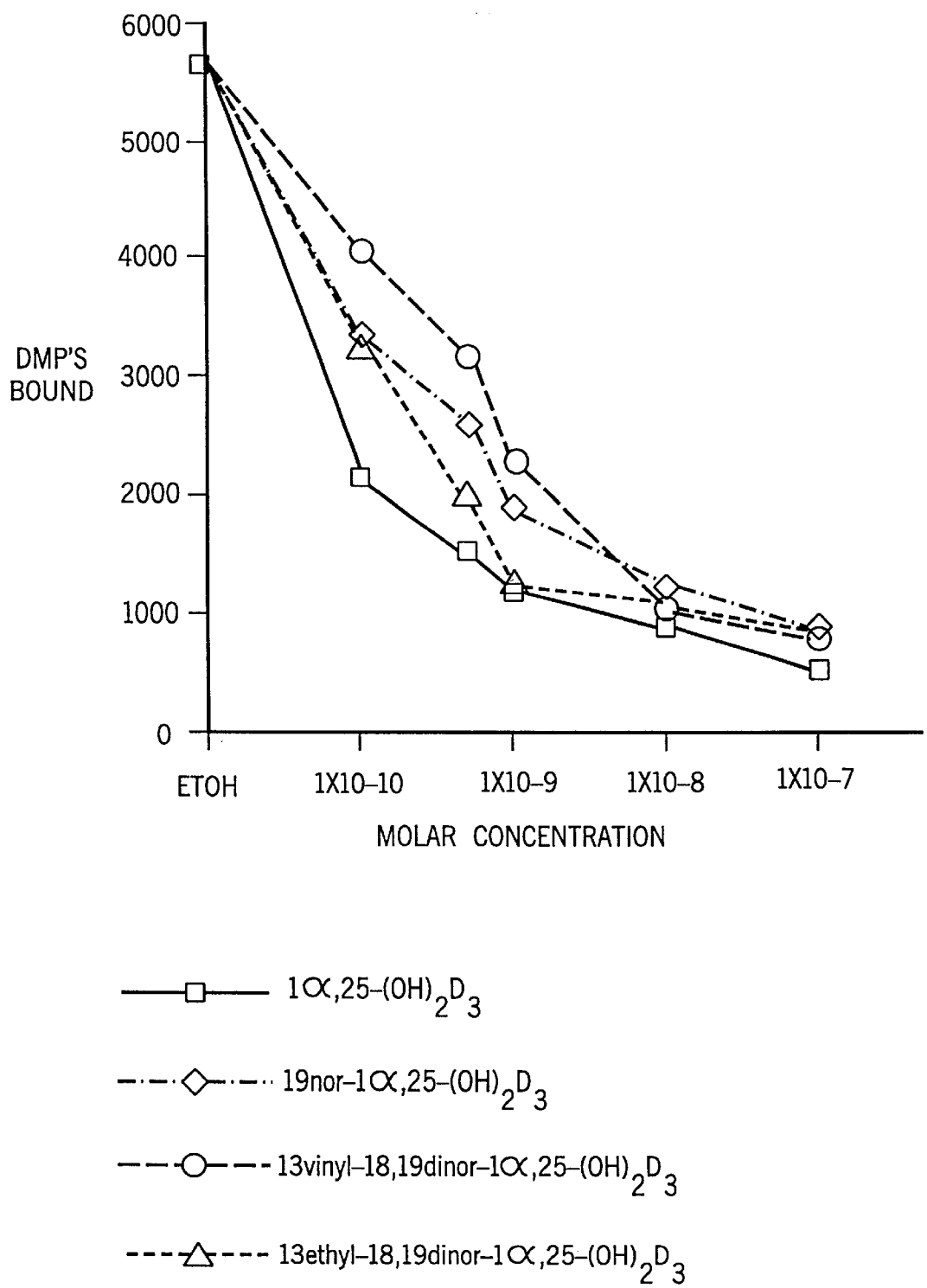
FIG. 1 is a graph illustrating the relative activity of 13-ethyl-18,19-dinor-$1\alpha,25$-dihydroxyvitamin $D_3$, 13-vinyl-18,19-dinor-$1\alpha,25$-dihydroxyvitamin $D_3$, 19-nor-$1\alpha,25$-dihydroxyvitamin $D_3$ and $1\alpha,25$-dihydroxyvitamin $D_3$ to compete for binding of [3H]-1,25-$(OH)_2$-$D_3$ to the vitamin D pig intestinal nuclear receptor.

A series of $1\alpha$-hydroxylated vitamin D compounds comprising 19-nor-vitamin D analogs having a methyl or methylene group at the 18-position, i.e. 13-ethyl-18,19-dinor-vitamin D compounds and 13-vinyl-18,19-dinor-vitamin D compounds, particularly 13-ethyl-18,19-dinor-1α,25-dihydroxyvitamin $D_3$ and 13-vinyl-18,19-dinor-1α,25-dihydroxyvitamin $D_3$.

Structurally these novel analogs are characterized by the general formula I shown below:

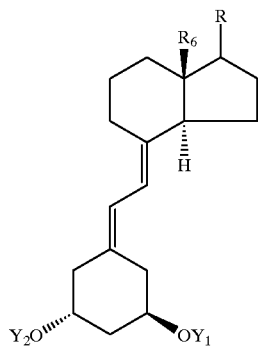

I where $Y_1$ and $Y_2$, which may be the same or different, are each selected from the group consisting of hydrogen and a hydroxy-protecting group, $R_6$ is selected from the group consisting of an ethyl or vinyl radical, and where the group R represents any of the typical side chains known for vitamin D type compounds.

More specifically R can represent a saturated or unsaturated hydrocarbon radical of 1 to 35 carbons, that may be straight-chain, branched or cyclic and that may contain one or more additional substituents, such as hydroxy- or protected-hydroxy groups, fluoro, carbonyl, ester, epoxy, amino or other heteroatomic groups. Preferred side chains of this type are represented by the structure below

where the stereochemical center (corresponding to C-20 in steroid numbering) may have the R or S configuration, (i.e. either the natural configuration about carbon 20 or the 20-epi configuration), and where Z is selected from Y, —OY, —$CH_2OY$, —C≡—CY and —CH=CHY, where the double bond may have the cis or trans geometry, and where Y is selected from hydrogen, methyl, —$COR^5$ and a radical of the structure:

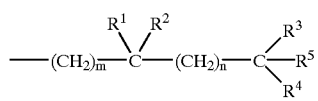

where m and n, independently, represent the integers from 0 to 5, where $R^1$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R^1$ and $R^2$, taken together, represent an oxo group, or an alkylidene group, =$CR^2R^3$, or the group —$(CH_2)_p$—, where p is an integer from 2 to 5, and where $R^3$ and $R^4$, taken together, represent an oxo group, or the group —$(CH_2)_q$—, where q is an integer from 2 to 5, and where $R^5$ represents hydrogen, hydroxy, protected hydroxy, or $C_{1-5}$ alkyl and wherein any of the CH-groups at positions 20, 22, or 23 in the side chain may be replaced by a nitrogen atom, or where any of the groups —CH($CH_3$)—, —CH($R^3$)—, or —CH($R^2$)— at positions 20, 22, and 23, respectively, may be replaced by an oxygen or sulfur atom.

The wavy line to the substituent at C-20 indicates that the carbon 20 may have either the R or S configuration.

Specific important examples of side chains with natural 20R-configuration are the structures represented by formulas (a), b), (c), (d) and (e) below. i.e. the side chain as it occurs in 25-hydroxyvitamin $D_3$ (a); vitamin $D_3$ (b); 25-hydroxyvitamin $D_2$ (c); vitamin $D_2$ (d); and the C-24 epimer of 25-hydroxyvitamin $D_2$ (e):

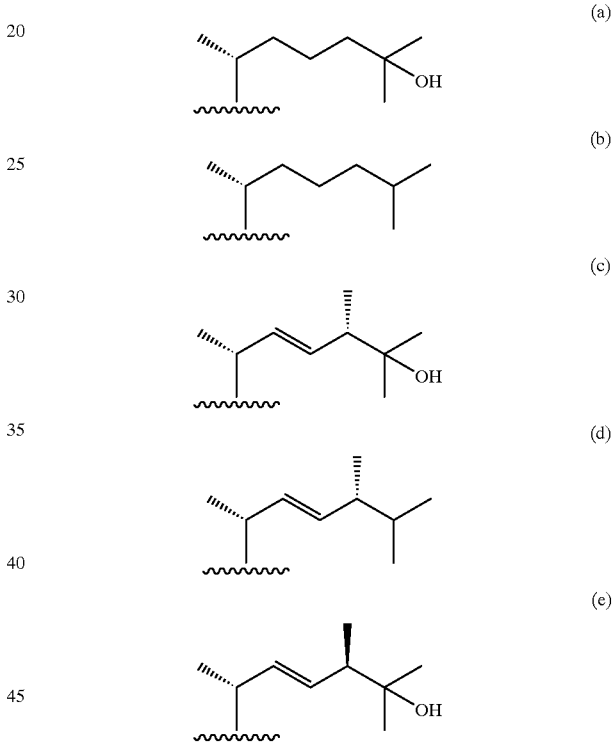

The preferred compounds are 13-ethyl-18,19-dinor-1α, 25-dihydroxyvitamin $D_3$ and 13-vinyl-18,19-dinor-1α,25-dihydroxyvitamin $D_3$.

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies a group of the type Q CO—, where Q represents hydrogen or a hydrocarbon radical of from 1 to 18 carbons that may be straight chain, cyclic, branched, saturated or unsaturated. Thus, for example, the hydrocarbon radical Q may be a straight chain or branched alkyl group, or a straight chain or branched alkenyl group with one or more double bonds, or it may be an optionally substituted cycloalkyl or cycloalkenyl group, or an aromatic group, such as substituted or unsubstituted phenyl, benzyl or naphthyl. Especially preferred acyl groups are alkanoyl or alkenoyl groups, of which some typical examples are formyl, acetyl, propanoyl, hexanoyl, isobutyryl, 2-butenoyl, palmitoyl or oleoyl. The word "alkyl" as used in the description or the claims, denotes a straight-chain or branched alkyl radical of 1 to 10 carbons, in all its isomeric forms. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatized or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively.

It should be noted in this description that the term "24-homo" refers to the addition of one methylene group and the term "24-dihomo" refers to the addition of two methylene groups at the carbon 24 position in the side chain. Likewise, the term "trihomo" refers to the addition of three methylene groups. Also, the term "26,27-dimethyl" refers to the addition of a methyl group at the carbon 26 and 27 positions so that for example $R^3$ and $R^4$ are ethyl groups. Likewise, the term "26,27-diethyl" refers to the addition of an ethyl group at the 26 and 27 positions so that $R^3$ and $R^4$ are propyl groups.

In the following lists of compounds, the particular group attached at the carbon 13 position should be added to the nomenclature. For example, if a vinyl group is attached, the term "13-vinyl" should precede each of the named compounds. If an ethyl group is attached, the term "13-ethyl" should precede each of the named compounds. In addition, if the methyl group attached at the carbon 20 position is in its epi or unnatural configuration, the term "20(S)" or "20-epi" should be included in each of the following named compounds. The named compounds could also be of the vitamin $D_2$ or $D_4$ type if desired.

Specific and preferred examples of the 13-alkyl-compounds of structure I when the side chain is unsaturated are:

18,19-dinor-24-homo-1,25-dihydroxy-22-dehydrovitamin $D_3$;
  18,19-dinor-24-dihomo-1,25-dihydroxy-22-dehydrovitamin $D_3$;
  18,19-dinor-24-trihomo-1,25-dihydroxy-22-dehydrovitamin $D_3$;
18,19-dinor-26,27-dimethyl-24-homo-1,25-dihydroxy-22-dehydrovitamin $D_3$;
18,19-dinor-26,27-dimethyl-24-dihomo-1,25-dihydroxy-22-dehydrovitamin $D_3$;
18,19-dinor-26,27-dimethyl-24-trihomo-1,25-dihydroxy-22-dehydrovitamin $D_3$;
18,19-dinor-26,27-diethyl-24-homo-1,25-dihydroxy-22-dehydrovitamin $D_3$;
18,19-dinor-26,27-diethyl-24-dihomo-1,25-dihydroxy-22-dehydrovitamin $D_3$;
18,19-dinor-26,27-diethyl-24-trihomo-1,25-dihydroxy-22-dehydrovitamin $D_3$;
18,19-dinor-26,27-dipropoyl-24-homo-1,25-dihydroxy-22-dehydrovitamin $D_3$;
18,19-dinor-26,27-dipropyl-24-dihomo-1,25-dihydroxy-22-dehydrovitamin $D_3$; and
18,19-dinor-26,27-dipropyl-24-trihomo-1,25-dihydroxy-22-dehydrovitamin $D_3$.

Specific and preferred examples of the 13-alkyl-compounds of structure I when the side chain is saturated are:

18,19-dinor-24-homo-1,25-dihydroxyvitamin $D_3$;
18,19-dinor-24-dihomo-1,25-dihydroxyvitamin $D_3$;
18,19-dinor-24-trihomo-1,25-dihydroxyvitamin $D_3$;
18,19-dinor-26,27-dimethyl-24-homo-1,25-dihydroxyvitamin $D_3$;
18,19-dinor-26,27-dimethyl-24-dihomo-1,25-dihydroxyvitamin $D_3$;
18,19-dinor-26,27-dimethyl-24-trihomo-1,25-dihydroxyvitamin $D_3$;
18,19-dinor-26,27-diethyl-24-homo-1,25-dihydroxyvitamin $D_3$;
18,19-dinor-26,27-diethyl-24-dihomo-1,25-dihydroxyvitamin $D_3$;
18,19-dinor-26,27-diethyl-24-trihomo-1,25-dihydroxyvitamin $D_3$;
18,19-dinor-26,27-dipropyl-24-homo-1,25-dihydroxyvitamin $D_3$;
18,19-dinor-26,27-dipropyl-24-dihomo-1,25-dihydroxyvitamin $D_3$; and
18,19-dinor-26,27-dipropyl-24-trihomo-1,25-dihydroxyvitamin $D_3$.

Specific and preferred examples of the 13-alkyl-compounds of structure I when the side chain is shortened are:

18,19-dinor-24-nor-1,25-dihydroxyvitamin $D_3$;
18,19-dinor-23,24-nor-1,25-dihydroxyvitamin $D_3$;
18,19-dinor-1α-hydroxy-bishomopregnacholecalciferol; and
18,19-dinor-1α-hydroxy-homopregnacalciferol.

Examples of other side chains (e.g. hydroxyalkylated analogs) within the scope of the present invention can be found in Ostrem et al, "Induction of Monocytic Differentiation of HL-60 Cells by 1,25-Dihydroxyvitamin D Analogs," Jour. Bio. Chem., Vol 262, No. 29, pp. 14164–14171 (1987), as well as in Calverley et al, "Vitamin D," Antitumor Steroids, Academic Press: San Diego, pp. 193–270 (1992).

The preparation the 13-alkyl-18,19-dinor-vitamin D compounds having the structure I can be accomplished as follows. First of all, and referring to Scheme 1, we prepared CD-ring fragments and chose diol (1a) as a starting material obtained from ozonolysis of vitamin $D_2$ followed by reduction with sodium borohydride and then selective tosylation of (1a) generated monotosylated (1b). Considering that the axial hydroxy group at $C_8$ in compound (1) is quite hindered and can withstand a variety of reaction conditions, even without protection of $C_8$-βOH, we directly introduced the side chain into the compound (1b) with six moles lithium salt of 3-methyl-1-butyn-3yl tetrahydropyranyl ether and catalytically hydrogenated the acetylenic bond in the side chain (2) with 10% Palladium-on-carbon to give compounds (2) and (3), respectively in high yield. Oxidation of (3) with pyridinium chlorochromate in the presence of sodium acetate gave 25-hydroxylated Windaus-Grundmann ketone derivative (8) in 56% overall yield from diol (1a) through 4 steps.

With the compound (3) in hand, our attention was next turned to extend one more carbon atom onto $C_{13}$. Taking advantage of an axil 8β-hydroxy-CD-synthon (3), we irradiated a mixture of (3), lead tetracetate, iodine, calcium carbonate in cyclohexane and unexpectantly found a mixture of diostereoisomers of the hemiacetal acetate (4), which proved to be a faster entry for making 18-substuted CD-ring synthons. Thus hydrolysis of (4) with potassium carbonate in methanol yield hemiacetals (5), which were submitted in a Wittig reaction by treatment of methyltriphenylphosphonium bromide and potassium tert-butoxide affording (6). Catalytic hydrogenation of (6) formed the compound (7). As with compound (3), both (6) and (7) were oxidized to the $C_{13}$-vinyl or $C_{13}$-ethyl-CD-ring synthon (9) and (10), respectively.

Finally, and referring now to Scheme 2, the compound 13 (a, b and c) were achieved by the sequences of the Horner-Wittig coupling of the phosphine oxide (14) with the ketone (8), (9) or (10) to give the compound 11 (a, b, and c). Thereafter, cleavage of the silyl group with tetrabutyl ammonium fluoride gave 12 (a, b, and c) and the removal of the alcohol protective group of compound 12 (a, b, and c) with p-toluensulfonic acid monhydrate gave compounds 13 (a, b, and c).

Although the above synthesis is specific to the preparation of the 13-vinyl-18,19-dinor-1α,25-dihydroxyvitamin $D_3$ and the 13-ethyl-18,19-dinor-1α,25-dihydroxyvitamin $D_3$, 13-vinyl and 13-ethyl compounds having varying side chains may also be prepared by this process. This is accomplished by the analogous coupling of phosphine oxide (14) with a ketone (9) or (10) having the appropriate side chain directly introduced into compound (1b) as described above.

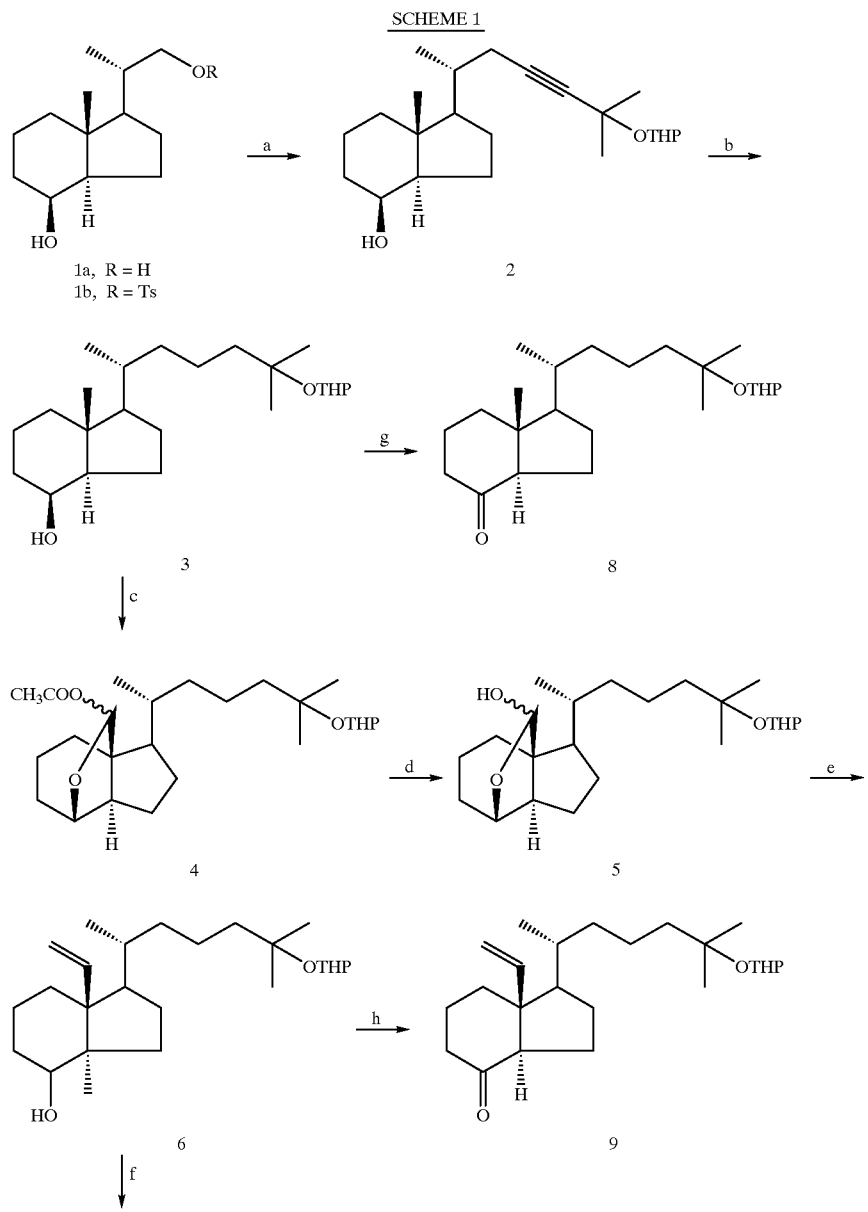

SCHEME 1

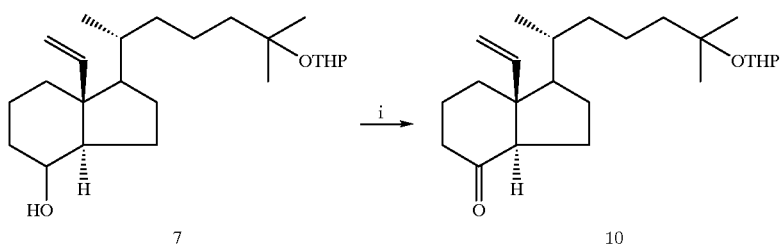

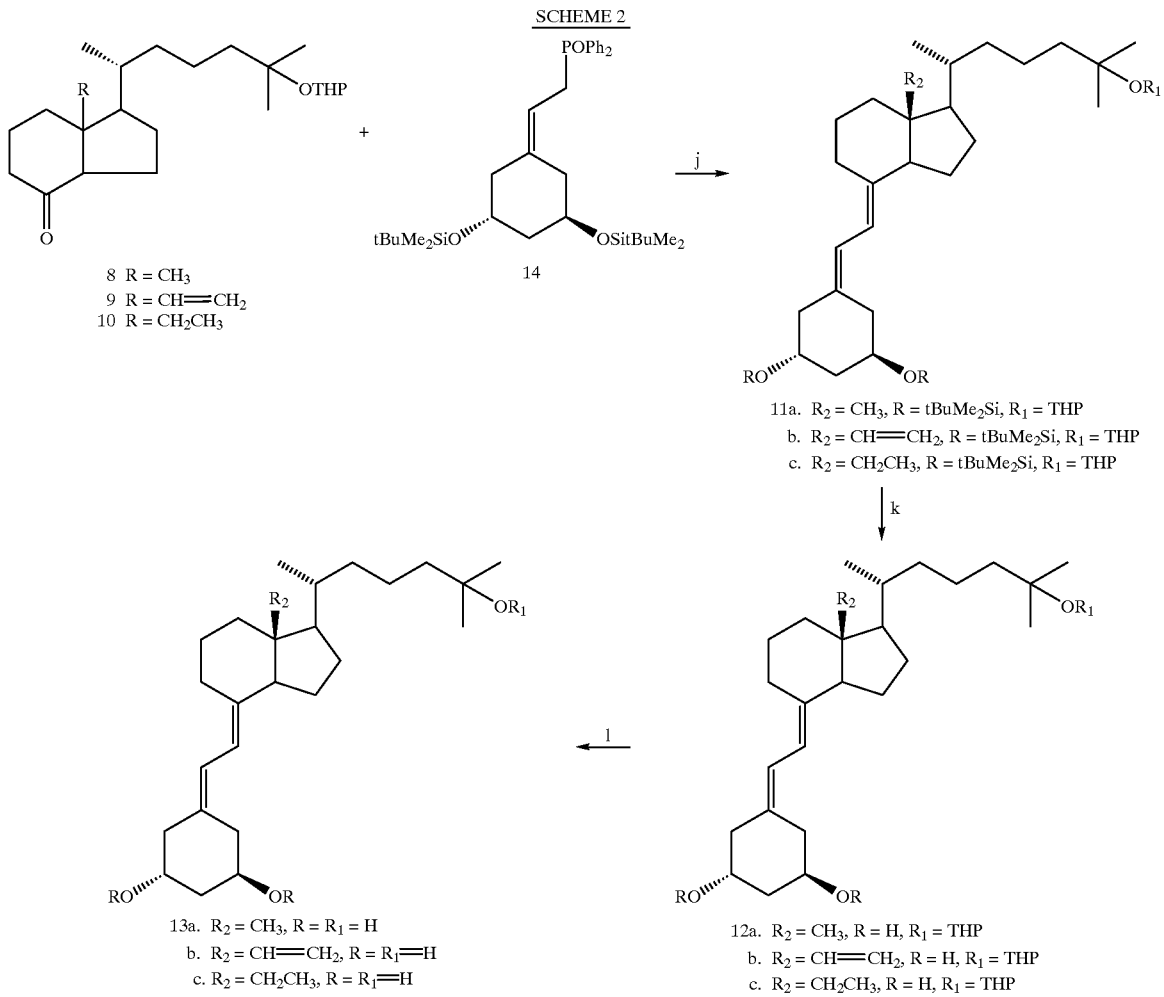

(j). n-BuLi, 11a, 48.5%, b. 56.73%, c. 69.6% (k) [CH$_3$(CH$_2$)$_3$]$_4$NF, 12a, 86.6%; b. 75.8%, c, 88.6%; (I) CH$_3$C$_6$H$_4$SO$_3$H——H$_2$O, 13a, 91%; b,75%, c, 69%.

Experimental

Spectra were obtained on the following instruments: Ultraviolet (UV) absorption spectra were taken with Perkin-Elmer Lambda 3B UV/VIS spectrophotometer. Nuclear magnetic resonance (NMR) spectra were recorded in CDCl$_3$ at 400 or 500 MHz with Bruker DMX spectrometer and at 200 MHz with Bruker WP 200SY–PCNMR+Version 1.01. Chemical shifts (δ) are reported downfield from internal Me$_4$Si (δ 0.00). Low Mass spectra were recorded at 70 eV on a Kratos MS-50 TC instrument equipped with a Kratos DS-55 data system. HRMS were recorded on Kratos MS-80 RFA with DS 55/D290. Flash chromatographic purification were carried out with 'Baker' silica gel 40 μm.

[1R-[1β (R*), 3aα, 4β, 7aβ]-Octahydro-1-[[2-tosyloxy]-1-methylethyl]-7a-methyl-1H-idene-4-ol (1b) To the stirred solution of diol (1a) (o.49 g, 2.3 mmol) in dry pyridine (10 ml) was added p-toluenesulfonyl chloride (665 mg, 3.49 mmol) at 0° C. The reaction mixture was stirred at 0° C. overnight. Then ice was added and the suspension was extracted with ethyl acetate. The extracts were washed with 7% hydrochloric acid, brine and dried over sodium sulfate. After removal of the solvent, the crude was purified by flash chromatography (20% EtOAC in hexane) to give the product (1b) 0.79 g in 94% yield. m. p. 94° C.

[1R-[1β (R*), 3aα4β, 7aβ]-Octahydro-1-[5-[[tetrahydro-2H-pyran-2-yl]-oxy]-1,5-dimethyl-3-hexynyl]-7a methyl-1

H-inden-4-ol (2). To a solution of 3-methyl-1-butyn-3yl-tetrahydropyranyl ether (1.52 g, 9.05 mmol) in anhydrous dioxane (20 ml, distilled from sodium) under argon at 5° C. was added dropwise 1.5 M n-butyllithium in hexane (6 ml) over 7 min. The slightly turbid mixture was stirred 0.5 h at 5° C. and 2 h at room temperature. Then monotosylate (1b) (0.53 g. 1.45 mmol) in anhydrous dioxane (4 ml) was added slowly over 5 min. into the turbid solution. Then it was refluxed for 50 h. The cooled pale brown suspension was poured into the cold 2 ml of 10% sodium bicarbonate solution, then extracted with ethylacetate. The combined extracts were washed with brine, dried over sodium sulfate and the solvent evaporated under reduced pressure. The residue was purified by flash chromatography (15% EtOAC in hexane) to afford the product (2) (0.43 g, 82% yield). $^1$H NMR(200 MHz,) δ:0.95 (S, 3H, $C_{7a}$—$CH_3$), 1.05 (d, J=8 Hz, 3H, $C_1CH_3$ side chain), 1.47, 1.51 (S, 6H, $C_5$—$C_3$ side chain), 3.49, 3.95 (m, 2H—$OCH_2$(THP)), 4.09 (m, 1H, $C_4$—H), 5.05 (d,J=2 Hz, —OCHO—). MS m/z 362 ($M^+$, 16), 347 ($M^+$—$CH_3$, 44), 341 (35), 325 (100), 307 (49), 301 (14).

[1R-[1β(R*), 3aα, 4β, 7aβ,]]-Octahydro-1-[5-[[tetrahydro-2H-Pyran-2-yl]-oxy]-1,5-dimethyl-hexyl]-7a methyl-1H-inden-4-ol(3). A mixture of compound (2) (0.32 g, 0.88 mmol) in methanol (8 ml), sodium hydrogen carbonate (15 mg) and 10% palladium-on-carbon (93 mg) was stirred under one atmosphere of hydrogen at room temperature until hydrogenation was complete (48 h). The catalyst was removed by filtration and the solvent was removed under reduced pressure. The residue was purified by flash chromatography (10% EtOAC in hexane) to afford the product (3) (0.27 g, 84% yield). $^1$H NMR (400 MHz) δ:0.9 (d, J=8 Hz, 3H, $C_1$—$CH_3$ side chain), 0.93 (S, 3H, $C_{7a}$—$CH_3$), 1.19, 1.20 (S, 6H, $C_5$—$CH_3$ side chain), 3.44, 3.95 (m, 2 H, —$OCH_2$(THP)), 4.07 (m, 1H, $C_4$—H), 4.71 (d, J=8 Hz, 1H, —OCHO—). MS: m/z, 366 ($M^+$, 8), 348 ($M^+$—$H_2O$, 13), 330 ($M^+$—$2H_2O$, 5), 308 ($M^+$, 100).

[1R-[1β(R*), 3aα, 4β, 7aβ,]] Octahydro-1-[5-[[tetrahydro-2H-pyran-2-yl]-oxy]-1,5-dimethyl hexyl]-7a methyl-4H-iden-4-one (8). To the suspension of pyridinium chlorochromate (32.6 mg, 0.15 mmol) and sodium acetate (23.9 mg, 0.29 mmol) in anhydrous dichloromethane (0.2 ml) was added the compound (3) (25.7 mg, 0.07 mmol) in dichloromethane (0.4 ml) in one portion at room temperature. The stirred solution became dark brown. After one hour, the reaction was complete. Then absolute ether was added and the mixture was filtered by suction. The black residue was washed with ether several times. After removal of the solvent, the crude was purified by flash chromatograph (5% EtOAC in hexane) to give the product (8) (22.2 mg, 86.85%). $^1$H NMR (400 MHz) δ:0.64 (S, 3H, $C_{7a}$—$CH_3$), 0.955(d. J=4 Hz. 3H, $C_1$—$CH_3$ side chain), 1.19, 1.21 (S, 6H, $C_5$—$CH_3$ side chain), 3.44, 3.95 (m, 2H, —$OCH_2$ (THP)), 4.705 (d, J=4 Hz, 1H, —OCHO—). MS: m/z 364 ($M^+$, 0.27), 263(51), 222(7), 151(26), 85(100).

Hemiacetal acetates (4). To a stirred mixture of compound (3) (86 mg, 0.235 mmol) in 25 ml cyclohexane, lead tetraacetate (547 mg, 1.23 mmol), calcium carbonate (97 mg, 0.97 mmol), under argon was added iodine (78 mg, 0.3 mmol) then the resulting mixture was refluxed with irradiation (300 watt) 5 h. After cooling, it was filtered, the residue was washed by cyclohexane. The combined filtrate was washed by 5% sodium thiosulfate, dried over sodium sulfate. After removal of the solvent, the residue was purified by flash chromatography (10% EtOAC in hexane) to obtain a mixture of two diosteroisomers (4) (72.4 mg, 73% yield). $^1$H NMR (500 MHz) δ:0.903 (d, J=7 Hz, 3H, $C_1$—$CH_3$ side chain), 0.949 (d, J=6.5 Hz, 3H, $C_1$—$CH_3$ side chain), 1.198 1.203 (S, 12H, $C_5$-side chain), 3.439, 3.955 (m, 4H, —$OCH_2$ (THP)), 4,241 (d, J=4.5 Hz, $C_4$—H), 4.431 (d, J=5 Hz, $C_4$—H), 4.696 (S, 2H, —OCHO—), 6.044, 6.083 (S, 2H, —$OCHOCOCH_3$). MS: m/z 363 (1,4), 321(7), 277(13), 261(71), 232(54), 219(30), 177(53), 121(73), 85(100).

Hemiacetals (5). A solution of compound (4) (71.4 mg, 0.169 mmol) in 0.8% potassium carbonate-methanol (1 ml) was stirred at room temperature 3 h. The solvent was removed by rotary evaporation and the residue was directly purified by flash chromatography (10% EtOAC in hexane) to give hemiacetals (5) (48 mg, 74.66%). $^1$H NMR (200 MHz) δ: 0.95,102 (d, J=6 Hz, 6H, $C_1$—$CH_3$ side chain), 1.18, 1.20 (S,12H, $C_5$—$CH_3$, side chain), 3.4 4, 3.96 (m, 4H, —$OCH_2$(THP)), 4.16 (d, J=4 Hz, 1H, $C_4$—H), 4.39 (d, J=6 Hz, 1H, $C_4$—H), 4.69 (m, 2H, —OCHO—), 5.25 (d, J=4 Hz, -hemiacetal-H), 5.39 (d, J=6 Hz, -hemiacetal-H), 9.8 (S, 1H, —CHO). MS: 362 ($M^+$—$H_2O$, 21), 344 ($M^+$—$2H_2O$, 6), 334 (11), 316 (84), 304 (89), 296 (81), 279 (30), 261(47), 243 (14), 232 (46), 220 (14), 177 (23), 161(17), 148 (33), 121(96), 85 (100).

[1R-[1β(R*), 3aα, 4β, 7aβ]]-Octahydro-1-[5-[[tetrahydro-2H-pyran-2-yl]oxy]-1,5-dimethyl-hexyl]-7a vinyl-1-H inden-4-ol (6). A mixture of methytriphenylphosphonium bromide (144.5 mg, 0.404 mmol) in anhydrous THF (4 ml) and potassium tert-butoxide in THF (0.4 ml, 1.0 M) was refluxed under argon overnight (14 h) to get deep orange suspension. The hemiacetals (5) (48 mg, 0.126 mmol) in anhydrous THF (2 ml) was added into the cold suspension. Then the mixture was heated to reflux until the starting material almost disappeared. After removal of the solvent by rotary evaporation, cold 5% sodium bicarbonate (2 ml) was added. The resulting mixture was extracted with EtOAC. The combined extracts were dried over sodium sulfate, then the solvent was removed by rotary evaporation. The crude pale brown oil was purified by flash chromatography (10% EtOAC in hexane) to afford the product (6) (39.7 mg, 83% yield). $^1$H NMR (500 MHz) δ: 0.819 (d, J=5.5 Hz, 3H $C_1$—$CH_3$ side chain), 1.177, 1.193 (S, 6H, $C_5$—$CH_3$ side chain), 3.43, 3.92 (m, 2H, —$OCH_2$(THP)), 3.94 (m, 1H, $C_4$—H). 4.695 (d, J=6 Hz, —OCHO—), 5.26, 5.29 (dd, J=15 Hz, 10 Hz, 2H, $C_{7a}$—C=$CH_2$), 5.98, 601 (d,d J=15 Hz, 10 Hz, $C_{7a}$—CH=C). MS: m/z 378 ($M^+$, 63), 363 ($M^+$—$CH_3$, 42), 302(30), 276(36), 259(63), 233(19), 202 (26), 189(37), 175(100), 161(82).

[1R-[1β(R*), 3aα, 4, 7aα]]-Octahydro-1-[5-[[tetrahydro-2H-pyran-2-yl]-oxy]-1,5 dimethyl-hexyl]-7a-ethyl-1-H-inden-4-ol (7). To a stirred mixture of compound (6) (33 mg, 0.087 mmol) in methanol (1.5 ml) and sodium bicarbonate 3.9 mg), was added 10% Palladium-on-carbon (11.6 mg). Then it was stirred under one atmosphere of hydrogen at room temperature (48 h). The catalyst was removed by filter and washed with methanol. After removal of the solvent, the crude was purified by flash chromatography (5% EtOAC in hexane) to obtain the product (7) (25 mg, 75% yield). $^1$H NMR (200 MHz) δ: 0.91 (t, J=8 Hz, 3H, $C_{7a}$—$CCH_3$), 0.97 (d, J=6 Hz, 3H, $C_1$—$CH_3$), side chain), 1.19, 1.21 (S, 6H, $C_5$—$CH_3$ side chain), 2.13 (q, 2H, J=8 Hz, $C_{7a}$—$CH_2$-side chain), 3.44, 3.9 (m, 2H, —$OCH_2$ (THP)), 4.1 (m, 1H, $C_4$—H), 4.62 (m, 1H, —OCHO—). MS: m/z 380 ($M^{)+}$, 17), 362 ($M^+$—$H_2O$, 13), 344 (6), 333 ($M^+$—$H_2O$—$C_2H_5$, 7), 321(26), 304(36), 294(34), 278 ($M^+$—$C_5H_8O$—$H_2O$, 69), 261(100), 249(63).

[1R-[1β(R*), 3aα, 4β, 7aβ]]-Octahydro-1-[5-[[tetrahydro-2H-pyran-2-yl]-oxy]-1,5-dimethyl-hexyl]-7a-vinyl-4H-iden-4-one (9). Pyridinium chlorochromate (20.5 mg, 0.095 nmmol) and sodium acetate (17.5 mg, 0.21 mmol) were suspended in anhydrous dichloromethane (0.5 ml), then the compound (6) (17.7 mg, 0.0468 mmol) in $CH_2Cl_2$ (0.4 ml) was added in one portion at room temperature. The stirred solution turned to dark brown. After two and a half hour, pyridinium chlorochromate (39.6 mg) and sodium acetate (30.3 mg) was added again. Then it was stirred until the oxidation reaction was complete and worked-up as (8). The crude was purified by flash chromatography (6%EtOAC in hexane) to give the product (9) (14.8 mg, 84% yield). $^1$H NMR (400 MHz) δ: 0.95 (d, J=8 Hz, 3H, $C_1$—$CH_3$ side chain), 1.18, 1.20 (S, 6H, $C_5$—$CH_3$ side chain), 3.44, 3.94 (m, 2H, —$OCH_2$(THP)), 4.69 (d, J=4 Hz, 1H, —OCHO—), 5.04 (d, J=16 Hz, 1H, $C_{7a}$—C=CH), 5.20 (d, J=12 Hz, 1H, $C_{7a}$—C=CH), 5.48–5,56 (m, 1H, $C_{7a}$—CH=C—). MS: m/z 376 (M$^+$ 35), 359(14), 331(19), 318(100).

[1R-[1β(R*), 3aα, 4β, 7aβ]]-Octahydro-1-[5-[[tetrahydro-2H-pyran-yl]-oxy]-1,5-dimethyl-hexyl]-7a-ethyl-4H-iden-4-one (10). To the stirred suspension of pyridinium chlorochromate (28.5 mg, 0.132 mmol) and sodium acetate (22.6 mg, 0.28 mmol) in anhydrous $CH_2Cl_2$ (0.2 ml) was added the compound (7) (24 mg 0.063 mmol) in $CH_2Cl_2$ (0.4 ml) in one portion at room temperature. It became dark brown. After one and a half hour, the reaction was complete, then worked up to (8). The solvent was removed by rotary evaporation and the crude was purified by flash chromatography (2.5% EtOAC in hexane) to give the product (10) (21 mg, 88% yield). $^1$H NMR (400 MHz) δ: 0.9 (t, J=8 Hz, 3H, $C_{7a}$—$CH_3$) 1.025 (d, J=:4 Hz, 3H, $C_1$—$CH_3$ side chain). 1.19, 1.21 (S, 6H, $C_5$—H side chain), 2.28 (q. J=8 Hz, 2H, $C_{7a}$—$CH_2C$—), 3.44, 3.95 (m, J=4 Hz, 2H, —$OCH_2$ (THP)), 4.69 (m, 1H, —OCHO—). MS: m/z 378 (M$^+$, 4), 320 (M$^+$, 2.8), 294(1.4), 277(24), 247(26), 85(100).

1α, [(tert-butyldimethylsilyl)-oxyl, 25-[(tetrahydro-2H-pyran-2yl)-oxy]-19-nor-vitamin $D_3$ tert-butyldimethylsilyl ether (11a). To the solution of the phosphine oxide (14) (25.6 mg, 0.045 mmol) in anhydrous THF (0.5 ml) was treated dropwise under argon with 1.5 M n-butyllithium in hexane (0.04 ml), 0.06 mmnol) at −25° C. over 2 min. The resulting deep red solution was stirred for 20 min. Then the compound (8) (11 mg, 0.03 mmol) in anhydrous THF (0.3 ml) was added slowly at −75° C. The stirring was continued at −75° C. for 3 h. then overnight. After the addition of 10% sodium bicarbonate (2 ml) at −40° C., the reaction mixture was allowed to come to room temperature and extracted with ethylacetate. The combined organic extracts were dried over sodium sulfate. After removal of the solvent, the crude was purified by flash chromatography (2.5% EtOAC in hexane) to give the product (11a) (10.5 mg, 48.5% yield) and to recover the starting material (8) (3.5 mg) (7% EtOAC in hexane). $^1$H NMR (200 MHz) δ: 0.5 (S, 3H, $C_{18}$—$CH_3$), 0.81, 0.83 (S, 18H,—SiC(CH$_3$)$_3$ 0.87 (d, J=6 Hz, $C_{21}$—$CH_3$), 1.14, 1.16 (S, 6H, $C_{26,27}$—$CH_3$), 3.4, 3.9 (m, 2H, —$OCH_2$(THP)), 4.03 (m, 2H, $C_{3,5}$—CHOH), 4.65 (m, 1H, —OCHO—), 5.76 (d, J=10 Hz, $C_7$—H), $C_7$—H), 6.12 (d, J=10 Hz, $C_6$—H). MS: m/z 716 (M$^+$,40), 632 (M$^+$—$C_5H_8O$, 100), 614 (M$^+$—$C_5H_8O$—$H_2O$, 77), 590(15), 500(47), 476 (18), 446(32).

1α, [(tert-butyldimethylsilyl)-oxy], 25-[(tetrahydro-2H-pyran-2-yl)-oxy]-13-vinyl-18,19-dinor-vitamin $D_3$ tert-butyldimethylsilyl ether (11b). To the solution of phosphine oxide (14) (52.7 mg, 0.092 mmol) in anhydrous THF (0.3 ml) was treated dropwise under argon with 1.5M n-butyllithium in hexane (0.07 ml, 0.105 mmol) at −20° C. over 2 min. The resulting deep red solution was stirred 20 min. Then the compound (9) (11.2 mg, 0.03 mmol) was added slowly at −75° C. over 5 min. The stirring was continued at −75° C. 2 h and at −40° C. 6 h. After the addition of 10% sodium bicarbonate (1.5 ml) at −40° C., the reaction mixture was allowed to come to room temperature and extracted with EtOAC. The combined ethylacetate was dried over sodium sulfate. After removal of the solvent, the crude was purified by flash chromatography (3% EtOAC in hexane) to give the product (11 b) (12.3 mg, 56.73% yield). UV λ max ($C_2H_5OH$): 261.5 nm, 251.6 nm, 243.5 nm. $^1$H NMR (400 MHz) δ: 0.052, 0.054 (S, 12H, 2 Si(CH$_3$)$_2$ 0.86, 0.88 (S, 18H, 2 Si—Bu$^t$), 0.906 (d, J=5.6 Hz, 3H, $C_{21}$—$CH_3$), 1.185, 1.200 (S, 6H, $C_{26,27}$—$CH_3$). 3.449, 3.951 (m, 2H, —$OCH_2$(THP)). 4.066 (m, J=3.6 Hz, 2H, C3,5—CHOH), 4.695 (m, 1H, —OCHO—), 5.015 (d, J=18 Hz, 1H CH=C—), 5.12 (d, J=11.6 Hz, CH=C—), 5.40, 5.444 (dd, J=18 Hz, 11.6 Hz, 1H, C=CH—), 5.858 (d, J=11.2 Hz, 1H, $C_7$—H), 6.12 (d, J=11.2 Hz). MS: m/z 728 (M$^+$, 6.6), 644 (M$^+$—$C_5H_8O$, 64), 626 (M$^+$—$C_5H_8O$—$H_2O$, 70), 604 (28), 587(5), 569(15), 547(6), 512(5).

1α, [(tert-butyldimethylsilyl)-oxy], 25-[(tetrahydro-2H-pyran-2-yl)-oxy]-13-ethyl-18,19-dinor-vitamin $D_3$ tert-butyldimethylsilyl ether (11c). To the solution of phosphine oxide (14) (6.25 mg, 0.011 mmol) in anhydrous THF (0.3 ml) was treated dropwise under argon with 1.5M n-butyllithium in hexane (0.1 ml, 0.15 mmol) at −20° C. The resulting deep red solution was stirred for 20 min. Then the compound (10) (18 mg, 0.048 mmol) in THF (0.3 ml) was added slowly at −75° C. over 2 min. and the stirring was continued at −75° C. 2 h and at −40° C. 2 h. After the addition of 10% sodium bicarbonate (3 ml) at −40° C., the reaction mixture was allowed to come to room temperature and extracted with EtOAC. The combined organic extracts were dried over sodium sulfate. After removal of the solvent, the crude was purified by flash chromatography (3% EtOAC in hexane) to give the product (1 c) (24.2 mg, 69.6%). $^1$H NMR (200 MHz) δ: 0.75 (t, 3H, $C_{18}$—$CH_3$), 0.815, 0.824 (S, 18H, 2SiBu$^t$), 0.948 (d, J=6 Hz, 3H, $C_{21}$—$CH_3$) 1.148, 1.16 (S, 6H, $C_{26,27}$—$CH_3$), 2.75 (q.2H, $C_{18}$—$CH_2$) 3.4, 3.99 (m, 2H, —$OCH_2$ (THP)), 4.02 (m, 2H, $C_{3,5}$—CHOH), 4.65 (t, J=4 Hz, $^1$H, —OCHO—), 5.76 (d, J=12 Hz, 1H, $C_7$—H), 6.12 (d, J=12 Hz, 1H, $C_6$—H). MS: m/z 730 (M$^+$,9), 646 (M$^+$—$C_5H_8O$, 85), 628 (M$^+$—$C_5H_8O$—$H_2O$, 100).

1α-hydroxy,25-[(tetrahydro-2H-pyran-2yl)-oxy]-19-nor-vitamin $D_3$ (12a). To a solution of compound (11a) (9.5 mg, 0.013 mmol) in anhydrous THF (0.4 ml) was added 1M solution of tetrabutylammonium fluoride in THF (0.08 ml). The mixture was stirred under argon at 48–50° C. overnight. After removal of the solvent, the crude was purified by flash chromatography (50% EtOAC in hexane) to give the product (12a) (5.6 mg, 86.6% yield). $^1$H NMR (200 MHz) δ: 0.6 (S, 3H, $C_{18}$—$CH_3$), 0.925 (d, J=6 Hz, $C_{21}$-$CH_3$), 1.20, 1.21 (S, 6H, $C_{26,27}$—$CH_3$), 3.48, 3.95 (m, 2H, —$OCH_2$(THP)), 4.13, 4.17 (m, 2H, $C_{3,5}$—CHOH—), 4.7 (m, 1H—CHO—), 5.86 (d, J=12 Hz, $C_7$—H), 6.33 (d, J=12 Hz, $C_6$—H). MS: m/z 488 (M$^+$, 4), 404 (M$^+$—$C_5H_8O$, 40), 386 (M$^+$—$C_5H_8O$—$H_2O$, 63), 371 (M$^+$—$C_5H_8O$—$H_2O$—$CH_3$, 9) 275 (19).

1α-hydroxy,25-[(tetrahydro-2H-pyran-2yl)-oxy]-13-vinyl-18,19-dinor-vitamin $D_3$ (12b). To a solution of compound (11b) (12.3 mg, 0.017 mmol) in anhydrous THF (0.2 ml), was added 1 M solution of tetrabutylanmnonium fluorine in THF (0.2 ml). The mixture was stirred overnight under argon at 50° C. After removal of the solvent, the crude was purified by flash chromatography (50% EtOAC in hexane) to give the product (12b) (6.4 mg, 75.83% yield). UV λ max ($C_2H_5OH$): 261.1 nm, 251.2 nm. 243.5 nm. $^1$H NMR (200 MHz) δ:0.895 (d, J=6 Hz, 3H, $C_{21}$—$CH_3$). 1.185, 1.198 (S, 6H, $C_{26,27}$—$CH_3$), 3.44, 3.95 (m, 2H, —$OCH_2$(THP)), 4.14 (m, 2H, $C_{3,5}$—CHOH), 4.68 (m, 1H, —OCHO—), 4.97–5.17(m, 2H, —CH$_2$=C—), 5.36–5.51 (m, 1H, C=CH—), 5.89 (d, J=12 Hz, 1H, C$_7$—H), 6.28 (d, J=12 Hz, 1H, C$_6$—H). MS: m/z 500 (M$^+$, 6), 4.82 (M$^+$—H$_2$O, 2), 4.16 (M$^+$—C$_5$H$_8$O, 19), 398 (M$^+$—2H$_2$O—C$_5$H$_8$O, 67), 380 (M$^+$—3H$_2$O—C$_5$H$_8$O, 14).

1α-hydroxy,25-[(tetrahydro-2H-pyran-2yl)-oxy]-13-ethyl-18,19-dinor-vitamin D$_3$ (12c). To a solution of compound (11c) (22.5 mg, 0.031 mmol) in anhydrous THF (0.3 ml) was added 1M solution of tetrabutylammonium fluoride in THF (0.2 ml). The mixture was stirred overnight under argon at 50–54° C. Then an additional solution of tetrabutyammonium fluoride (0.01 ml) and 0.2 ml THF as added again. The mixture was stirred until no starting could be detected by t.l.c. After removal of the solvent, the crude was preferably flash chromatography (50% EtOAC in hexane) to give the product (12c) 13.7 mg, 88.6%). UV λ max (C$_2$H$_5$OH): 261.2 nm, 251.2 nm, 242.6 nm. $^1$H NMR (400 MHz) δ: 0.83 (t, J=8 Hz, 3H, C$_{18}$—CH$_3$), 1.00 8 Hz, 3H, C$_{21}$—CH$_3$), 120, 1.21 (S, 6H, C$_{26,27}$—CH$_3$), 2.75 (q. 2H, C$_{18}$—CH$_2$) 3.45, 3.95 (m, 2H, —OCH$_2$(THP)), 4.04, 4.12 (m, 2H, C$_{3,5}$—CHOH), 4.70 (m, 1H, —OCHO—), 5.84 (d, J=12 Hz, C$_7$—H), 6.32 (d, J=12 Hz, C$_6$—H). MS: m/z 502 (M$^+$, 3), 418 (M$^+$—C$_5$H$_8$O, 27), 400 (M$^+$—C$_5$H$_8$O—H$_2$O, 50), 371 (M$^+$—C$_5$H$_8$O—H$_2$O—C$_2$H$_5$__—, 17).

1α,25-dihydroxy-19-nor-vitamin D$_3$ (13a). To the solution of compound (12a) (5.6 mg, 0.011 mmol) in methanol (0.1 ml) was added p-toluensulfonic acid monohydrate (0.5 mg) under argon at 0–5° C. The mixture was stirred one hour. After addition of sodium carbonate (1.6 mg), the mixture was stirred 15 min. at 0° C., then concentrated under reduced pressure. The crude was purified by flash chromatography (70% EtOAC in hexane) to give the product (13a) (4.2 mg, 91%) m.p. 158–160° C., [α] D+72.93 (c=0.25 CHCl$_3$), UV$_{max}$(EtOH) 260.2 nm, 250.4 nm, 242.2 nm. $^1$H NMR (200 MHz) δ: 0.54 (S, 3H, C$_{18}$—CH$_3$), 0.93 (d, J=6 Hz, C$_{21}$—CH$_3$), 121, 1.22 (S, 6H, C$_{26,27}$—CH$_3$), 4.1 (m, 2H, C$_{3,5}$—CHOH), 5.83 (d, J=10 Hz, 1H, C$_7$—H), 6.3 1(d, J=10 Hz, 1H, C$_6$—H). MS: m/z 404 (M$^+$, 100), 386 (M$^+$—H$_2$O, 20), 371 (M$^+$—H$_2$O—CH$_3$, 16), 275 (34).

1α, 25-dihydroxy-13-vinyl-18,19-dinor-vitamin D$_3$ (13b). To the solution of compound (12b) (6.4 mg, 0.0128 mmol) in methanol (0.2 ml) was added p-toluensulfonic acid monohydrate (1.2 mg) under argon at 0.5° C., and the mixture was stirred one hour. After addition of sodium carbonate (1.1 mg), the mixture was stirred 15 min. at 0° C., then concentrated under reduced pressure. The crude was purified by flash chromatography (75% EtOAC in hexane) to give the product (13b) (4 mg, 75% yield). UV λ max (C$_2$H$_5$OH): 260.7 nm, 251.4 nm, 242.6 nm. [α]$_D$–9.64 (c=0.35, CHCl$_3$). $^1$H NMR (500 MHz): δ: 0.0914 (d, J=6 Hz, 3H, C$_{21}$—CH$_3$), 1.21 (S, 6H, C$_{26,27}$—CH$_3$), 4.045, 4.16 (m, 2H, C$_{3,5}$—CHOH), 5.017 (d, J=17.5 Hz, 1H, CH=C—), 5.153 (d, J=10 Hz, 1H CH=C—), 5.404–5.462(m, 1H, C=CH—), 5.896 (d, J=11 Hz, 1H, C$_7$—H), 6.27 (d, J=11 Hz, 1H, C$_6$—H). HRMS: m/z Calc. for C$_{27}$H$_{44}$O$_3$ (M$^+$, 416.3290); Found (M$^+$, 416.3321, 14.56), 398,3206(M$^+$—H$_2$O, 14.95), 365.2974 (M$^+$—2H$_2$O—CH$_3$, 1.695). 362.2892 (M$^+$—3H$_2$O, 1.023).

1α,25-dihydroxy-13-ethyl-18,19-dinor-vitamin D$_3$ (13c). To the solution of compound (12c) (13.4 mg, 0.027 mmol) in methanol (0.2 ml) was added p-toluensulfonic acid monohydrate (2.4 mg) at 0° C. and the mixture was stirred 75 min. under argon. After the reaction was complete, sodium carbonate (1.6 mg) was added and the mixture was stirred 15 min. at 0° C. again. Then the solvent was removed and the crude was purified by flash chromatography (80% EtOAC in hexane) to give the product (13c) (7.7 mg, 69%), m.p. 135–137° C., UV λ max (EtOH), 260.9 nm, 250.9 nm (Σ=33612), 242.4 nm, [a]$_D$+40.45 (c=0.66, CHCl$_3$). $^1$H NMR (400 MHz) d: 0.83 (t, J=8 Hz, 3H, C$_{18}$—CH$_3$), 1.01 (d, J=8 Hz, 3H, C$_{21}$—CH$_3$), 1.22 (S, 6H, C$_{26,27}$—CH$_3$), 2.75 (m, J=8 Hz, 2H, C$_{18}$—CH$_2$), 4.10, 4.14 (m, J=8 Hz, 2H, C$_{3,5}$—CHOH), 5.85 (d, J=12 Hz, 1H, C$_7$—H), 6.32 (d, J=12 Hz, 1H, C$_6$—H). HRMS: m/z Calc. for C$_{27}$H$_{46}$O$_3$ (M$^+$, 418.3447); Found 418.3451 (M$^+$, 25.34), 400.3346 (M$^+$—H$_2$O, 22.64), 382.3249 (M$^+$—2H$_2$O, 2.97), 367.2968 (M$^+$—2H$_2$O—CH$_3$, 2.56).

BIOLOGICAL ACTIVITY OF 13-ETHYL AND 13-VINYL-18,19-DINOR-1,25-(OH)$_2$D$_3$ COMPOUNDS

The introduction of an ethyl or vinyl group to the 13-position of 18,19-dinor-1,25-(OH)$_2$D$_3$ increases binding to the porcine intestinal vitamin D receptor as compared to the standard 1,25-(OH)$_2$D$_3$ (FIG. 1). In fact, at low concentrations the 13-ethyl and 13-vinyl 18,19-dinor-1α,25-dihydroxyvitamin D$_3$ compounds have approximately twice the binding activity of 1,25-(OH)$_2$D$_3$. It might be expected from these results that the 13-ethyl and 13-vinyl compounds would have greater biological activity than 1α,25-(OH)$_2$D$_3$. Surprisingly, however, the 13-ethyl and 13-vinyl substitutions produced analogs with no significant change versus control in intestinal calcium transport activity or bone calcium mobilizing activity. When given for 7 days in a chronic mode, the compounds tested resulted in little if any effects on calcium metabolism (Table 1), and in fact, the activity of these two compounds on bone calcium mobilization (serum calcium) and intestinal calcium transport was minimal and about equal to that of 19-nor-1,25-(OH)$_2$D$_3$. These results illustrate that the 13-ethyl and 13-vinyl derivatives of 18,19-dinor-1,25-(OH)$_2$D$_3$ have minor if any action on the mobilization of calcium from bone or on intestinal calcium absorption.

Figure 2:
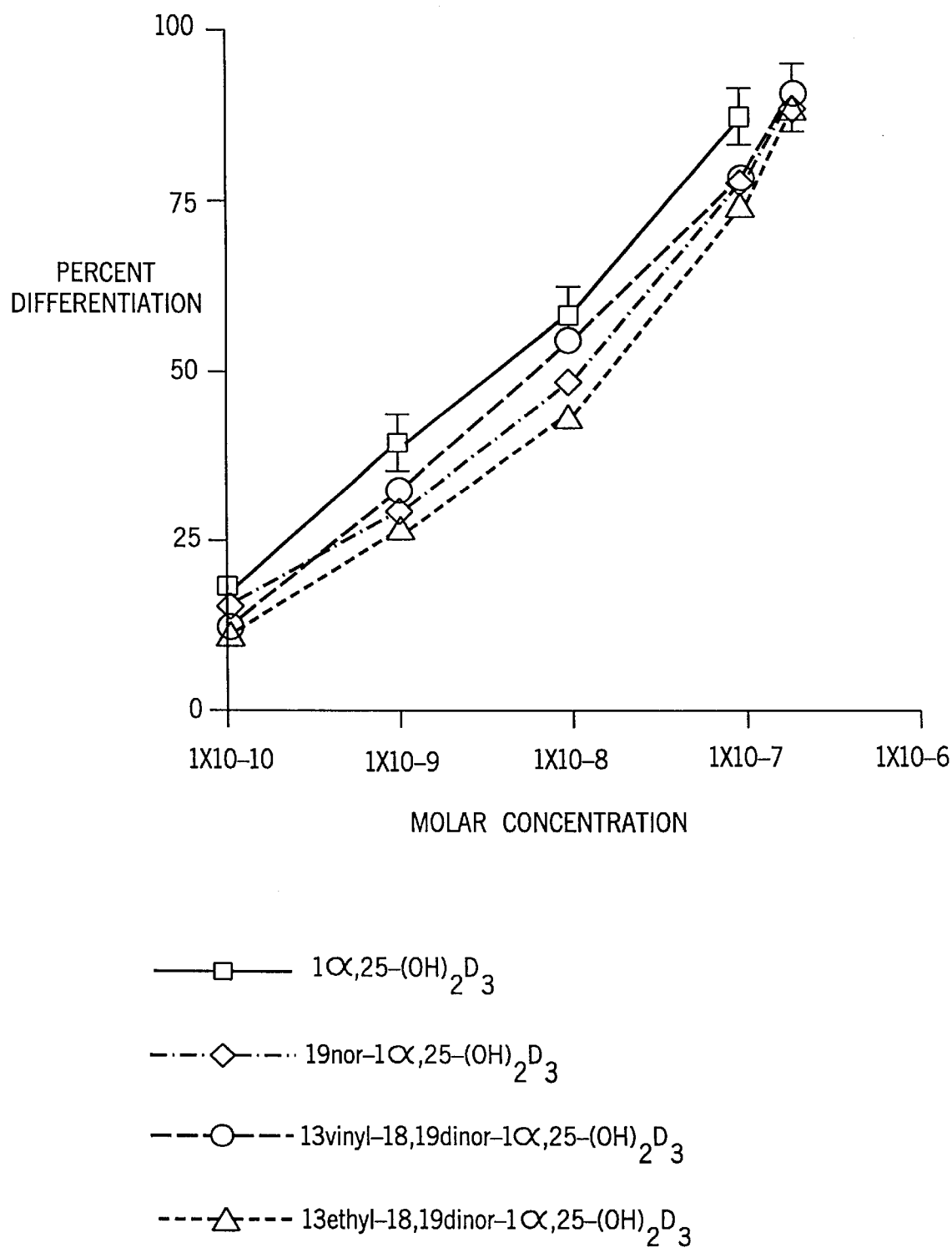
FIG. 2 is a graph illustrating the percent HL-60 cell differentiation as a function of the concentration of 13-ethyl-18,19-dinor-$1\alpha,25$-dihydroxyvitamin $D_3$, 13-vinyl-18,19-dinor-$1\alpha,25$-dihydroxyvitamin $D_3$, 19-nor-$1\alpha,25$-dihydroxyvitamin $D_3$ and $1\alpha,25$-dihydroxyvitamin $D_3$.

The results in FIG. 2 illustrate that the 13-ethyl and 13-vinyl derivatives of 18,19-dinor-1,25-(OH)$_2$D$_3$ are extremely potent in inducing differentiation of HL-60 cells to the monocyte. The 13-ethyl and 13-vinyl derivatives of 18,19-dinor-1α,25-(OH)$_2$D$_3$ compounds had activity similar to 1,25-(OH)$_2$D$_3$. These results illustrate the potential of the 13-ethyl and 13-vinyl derivatives of 18,19-dinor-1α,25-(OH)$_2$D$_3$ compounds as anti-cancer agents, especially against leukemia, colon cancer, breast cancer and prostate cancer, or as agents in the treatment of psoriasis.

Competitive binding of the analogs to the porcine intestinal receptor was carried out by the method described by Dame et al (Biochemistry 25, 4523–4534, 1986).

The differentiation of HL-60 promyelocytic into monocytes was determined as described by Ostrem et al (J. Biol. Chem. 262, 14164–14171, 1987).

TABLE 1

Response of Intestinal Calcium Transport and Serum Calcium (Bone Calcium Mobilization) Activity to Chronic Doses of 13-Ethyl and 13-Vinyl Derivatives of 18,19-Dinor-1,25-(OH)$_2$D$_3$

| Group | Dose (pmol/day/7 days) | Intestinal Calcium Transport (S/M) | Serum Calcium (mg/100 ml) |
|---|---|---|---|
| Vitamin D Deficient | Vehicle | 3.34 ± 0.33 | 3.57 ± 0.07 |
| 19-Nor-1,25-(OH)$_2$D$_3$ | 260 | 4.02 ± 0.50 | 3.83 ± 0.20 |
| 13-Ethyl-18,19-Dinor-1,25- | 260 | 4.30 ± 0.20 | 4.39 ± 0.53 |

TABLE 1-continued

Response of Intestinal Calcium Transport and
Serum Calcium (Bone Calcium Mobilization) Activity
to Chronic Doses of 13-Ethyl and 13-Vinyl
Derivatives of 18,19-Dinor-1,25-(OH)$_2$D$_3$

| Group | Dose (pmol/day/7 days) | Intestinal Calcium Transport (S/M) | Serum Calcium (mg/100 ml) |
|---|---|---|---|
| (OH)$_2$D$_3$ | 500 | 4.40 ± 0.27 | 3.99 ± 0.33 |
| 13-Vinyl-18,19-Dinor-1,25-(OH)$_2$D$_3$ | 260 | 4.02 ± 0.24 | 3.32 ± 0.21 |
|  | 500 | 4.25 ± 0.55 | 3.52 ± 0.12 |

Male weanling rats were obtained from Sprague Dawley Co. (Indianapolis, Ind.) and fed a 0.47% calcium, 0.3% phosphorus vitamin D-deficient diet for 1 week and then given the same diet containing 0.02% calcium, 0.3% phosphorus for 3 weeks. During the last week they were given the indicated dose of compound by intraperitoneal injection in 0.1 ml 95% propylene glycol and 5% ethanol each day for 7 days. The control animals received only the 0.1 ml of 95% propylene glycol, 5% ethanol. Twenty-four hours after the last dose, the rats were sacrificed and intestinal calcium transport was determined by everted sac technique as previously described and serum calcium determined by atomic absorption spectrometry on a model 3110 Perkin Elmer instrument (Nonvalk, Conn.). There were 5 rats per group and the values represent mean ±SEM.

For treatment purposes, the novel compounds of this invention defined by formula I may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds may be administered orally, topically, parenterally or transdermally. The compounds are advantageously administered by injection or by intravenous infusion or suitable sterile solutions, or in the form of liquid or solid doses via the alimentary canal, or in the form of creams, ointments, patches, or similar vehicles suitable for transdermal applications. Doses of from 0.1 µg to 50 µg per day of the compounds are appropriate for treatment purposes, such doses being adjusted according to the disease to be treated, its severity and the response of the subject as is well understood in the art. Since the new compounds exhibit specificity of action, each may be suitably administered alone, or together with graded doses of another active vitamin D compound—e.g. 1α-hydroxyvitamin D$_2$ or D$_3$, or 1α,25-dihydroxyvitamin D$_3$ —in situations where different degrees of bone mineral mobilization and calcium transport stimulation is found to be advantageous.

Compositions for use in the above-mentioned treatment of psoriasis and other malignancies comprise an effective amount of one or more 13-substituted-18,19-dinor-vitamin D compound as defined by the above formula I as the active ingredient, and a suitable carrier. An effective amount of such compounds for use in accordance with this invention is from about 0.01 µg to about 100 µg per gm of composition, and may be administered topically, transdermally, orally or parenterally in dosages of from about 0.1 µg/day to about 100 µg/day.

The compounds are advantageously administered in amounts sufficient to effect the differentiation of promyelocytes to normal macrophages. The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For asthma treatment, inhalation of powder, self-propelling or spray formulations, dispensed with a spray can, a nebulizer or an atomizer can be used. The formulations, when dispensed, preferably have a particle size in the range of 10 to 100µ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:

1. A method of making a ketone of the formula

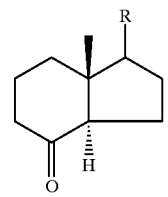

where R is represented by the structure:

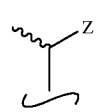

where the stereochemical center at carbon 20 may have the R or S configuration, and where Z is selected from Y, —OY, —CH$_2$OY, —C≡CY and —CH=CHY, where the double bond may have the cis or trans geometry, and where Y is selected from hydrogen, methyl, —COR⁵ and a radical of the structure:

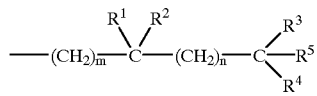

where m and n, independently, represent the integers from 0 to 5, where $R^1$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$ and $R^4$, independently is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R^1$ and $R^2$, taken together, represent an oxo group, or an alkylidene group, $=CR^2R^3$, or the group $—(CH_2)_p—$, where p is an integer from 2 to 5, and where $R^3$ and $R^4$, taken together, represent an oxo group, or the group $—(CH_2)_q—$, where q is an integer from 2 to 5, and wherein any of the CH-groups at positions 20, 22, or 23 in the side chain may be replaced by a nitrogen atom, or where any of the groups —CH(CH₃)—, —CH(R³)—, —CH(R²)— at positions 20, 22 and 23, respectively, may be replaced by an oxygen or sulfur atom, and further wherein $R^5$ is a protected-hydroxy group, which comprises the steps of selectively tosylating a diol of the formula

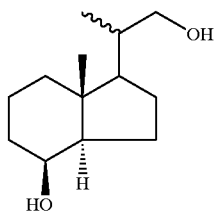

to obtain a mono-tosolyate of the formula

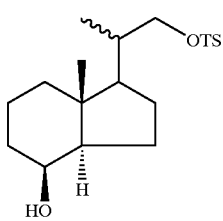

thereafter converting the mono-tosylate to an acetylenic compound having the formula

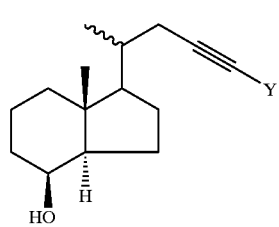

catalytically hydrogenating the acetylenic bond to obtain a hydroxylated derivative of the formula

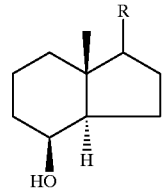

and oxidizing the hydroxylated derivative to said ketone.

2. The method of claim 1 wherein the step of oxidizing takes place with pyridinium chlorochromate in the presence of sodium acetate.

3. The method of claim 1 wherein the ketone made has the formula

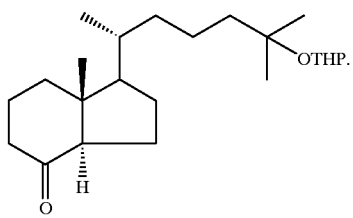

4. The method of claim 1 wherein the acetylenic compound has the formula

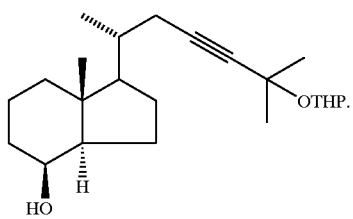

5. The method of claim 1 wherein the hydoxylated derivative has the formula

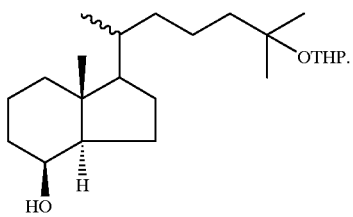

6. A compound having the formula:

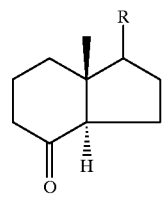

where the group R is represented by the structure:

where the stereochemical center at carbon 20 may have the R or S configuration, and where Z is selected from Y, —OY, —CH$_2$OY, —C≡CY and —CH=CHY, where the double bond may have the cis or trans geometry, and where Y is selected from hydrogen, methyl, —COR$^5$ and a radical of the structure:

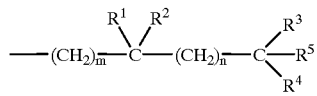

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$ and R$^4$, independently is selected from deuterium, deuteroalkyl, hydrogen, fluoro, trifluoromethyl and a straight-chain C$_{1-5}$ alkyl, which may optionally, bear a hydroxy or protected-hydroxy substituent, and where R$_1$ and R$^2$, taken together, represent an oxo group, or an alkylidene group, =CR$^2$R$^3$, or the group —(CH$_2$)$_p$—, where p is an integer from 2 to 5, and where R$^5$ represents a protected hydroxy group and wherein any of the CH-groups at positions 20, 22, or 23 in the side chain may be replaced by a nitrogen atom, or where any of the groups —CH(CH$_3$)—, —CH(R$^3$)—, or —CH(R$^2$)— at positions 20, 22, and 23, respectively, may be replaced by an oxygen or sulfur atom, with the proviso that R cannot be

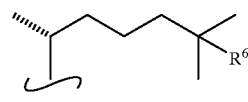

or

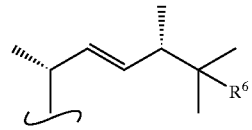

where R$^6$ is hydrogen, a hydroxy group, or a protected hydroxy group.

* * * * *